US00PP27052P3

(12) United States Plant Patent
Klemm et al.

(10) Patent No.: US PP27,052 P3
(45) Date of Patent: Aug. 9, 2016

(54) ***CALIBRACHOA* PLANT NAMED 'KLECA13248'**

(50) Latin Name: ***Calibrachoa* sp.**
Varietal Denomination: KLECA13248

(71) Applicant: Klemm+Sohn GmbH & Co. KG, Stuttgart (DE)

(72) Inventors: Nils Klemm, Stuttgart (DE); Anita Stöver, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 176 days.

(21) Appl. No.: 14/121,074

(22) Filed: Jul. 28, 2014

(65) Prior Publication Data

US 2016/0029536 P1 Jan. 28, 2016

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Keith Robinson
(74) *Attorney, Agent, or Firm* — Bethany R. Roahrig; Barbara Campbell; Cochran Freund & Young, LLC

(57) ABSTRACT

A new *Calibrachoa* plant particularly distinguished by having a red-purple flower color and a semi-trailing plant habit, is disclosed.

1 Drawing Sheet

Genus and species: *Calibrachoa* sp.
Variety denomination: 'KLECA13248'.

BACKGROUND OF THE NEW PLANT

The present invention comprises a new and distinct variety of *Calibrachoa*, botanically known as *Calibrachoa* sp., and hereinafter referred to by the variety name 'KLECA13248'. 'KLECA13248' originated from a controlled-cross between the female *Calibrachoa* variety 'KLECA08170' (U.S. Plant Pat. No. 21,061) and the proprietary male *Calibrachoa* variety 'CA-2008-0300' (unpatented).

In May 2009, two *Calibrachoa* parental lines, the female variety 'KLECA08170' and the male *Calibrachoa* variety 'CA-2008-0300' were crossed via a controlled cross in Stuttgart, Germany and seeds were obtained. The seeds were sown and plants were grown for evaluation. A plant line was selected in May 2010 which had a red-purple flower color and subsequently named 'KLECA13248'. In May 2010, 'KLECA13248' was first vegetatively propagated by tip cuttings in Stuttgart, Germany. 'KLECA13248' was found to reproduce true to type in successive generations of asexual propagation via tip cuttings.

SUMMARY

The following are the most outstanding and distinguishing characteristics of this new variety when grown under normal horticultural practices in Stuttgart, Germany.

1. Red-purple flower color; and
2. A semi-trailing plant habit.

DESCRIPTION OF THE PHOTOGRAPH

This new *Calibrachoa* plant is illustrated by the accompanying photograph which shows a close-up of the flowers. The photograph is of a five-month-old plant grown in a controlled greenhouse environment in Stuttgart, Germany in May 2012.

The colors shown are as true as can be reasonably obtained by conventional photographic procedures.

DESCRIPTION OF THE NEW VARIETY

The following detailed descriptions set forth the distinctive characteristics of 'KLECA13248'. The data which define these characteristics were collected from asexual reproductions carried out in Stuttgart, Germany. Data was collected on eleven-weeks-old plants grown in Stuttgart, Germany June 2014. Color references are to The R.H.S. Colour Chart of The Royal Horticultural Society of London (R.H.S.), 5$^{th}$ edition (2007).

Classification:
- *Family*.—Solanaceae.
- *Species*.—*Calibrachoa* sp.
- *Common name*.—*Calibrachoa*.
- *Parentage*.—Female: Proprietary female *Calibrachoa* 'KLECA081710'. Male: Proprietary male *Calibrachoa* 'CA-2008-0300' (unpatented).

Plant description:
- *Life cycle*.—Annual.
- *Form*.—Semi-trailing.
- *Habit*.—Semi-trailing.
- *Height (from soil line to top of foliage)*.—5.0 cm.
- *Spread*.—30.0 cm.

Propagation: Vegetatively propagated.
- *Type cuttings*.—Tip cuttings.
- *Time to initiate roots*.—5 days at approximately 20° Celsius.
- *Length of shoot cutting*.—4.5 cm.
- *Time to produce a rooted cutting*.—19 days.

Stems:
- *Stem color*.—RHS 146A.
- *Pubescence*.—Present.
- *Pubescence color*.—RHS 146C.
- *Stem diameter*.—0.3 cm.

*Stem length.*—15.0 cm. From soil line to first node: 1.3 cm. Total length: 16.3 cm.
*Internode length.*—2.0 cm.

Leaves:
*Arrangement.*—Alternate, simple, sessile.
*Shape.*—Broad elliptic.
*Apex.*—Obtuse to slightly acute.
*Base.*—Attenuate.
*Margin.*—Entire.
*Surface (both upper and lower surfaces).*—Smooth and glabrous.
*Surface pubescence.*—Absent.
*Variegation.*—Absent.
*Venation.*—Pinnate.
*Venation color.*—Upper surface: RHS 138A. Lower surface: RHS 138C.
*Length.*—2.7 cm.
*Width.*—1.2 cm.
*Color.*—Upper surface: RHS N137A. Lower surface: RHS 138B.
*Fragrance.*—Absent.
*Pedicel.*—Length: 1.2 cm. Diameter: 1.0 mm.

Flowers: Single flowers.
*Flowering habit.*—Flower attitude semi-erect, single, axillary.
*Flower type.*—Determinate inflorescence.
*Flowering requirements.*—A minimum of light sun is required.
*Duration of flowers.*—6 days.
*Corolla.*—Medium texture.
*Shape.*—Trumpet shaped.
*Fragrance.*—Absent.
*Degree of lobing.*—Weak.

Flower buds:
*Surface.*—Smooth.
*Length.*—2.0 cm.
*Diameter.*—0.6 cm.
*Shape.*—Irregular to oblong.
*Color.*—RHS N81A.

Peduncle:
*Length.*—1.2 cm.
*Diameter.*—0.1 cm.
*Color.*—RHS 144B.
*Texture.*—Smooth.
*Anthocyanin color.*—RHS N77C.

Flower description:
*Flower depth.*—2.8 cm.
*Flower tube length.*—1.6 cm.
*Flower tube diameter.*—1.1 cm.
*Flower diameter.*—3.6 cm.
*Pedicel color.*—RHS 144B.
*Calyx.*—Funnel-shaped.

Sepals:
*Shape.*—Lanceolate.
*Apex.*—Broad acute.
*Base.*—Fused.
*Margin.*—Entire.
*Length.*—1.5 cm.
*Diameter.*—0.4 cm.
*Texture (both upper and lower surfaces).*—Smooth.
*Sepal color.*—Upper surface: RHS 144A. Lower surface: RHS 146B.

Petals:
*Shape.*—Heart-shaped.
*Length.*—1.9 cm.
*Apex.*—Obverse.
*Margin.*—Entire, weak undulation.
*Base.*—Open and fused in the tube.
*Pubescence.*—Absent.
*Texture (both upper and lower surfaces).*—Smooth.
*Lobe length.*—1.8 cm.
*Lobe width.*—1.8 cm.
*Color.*—Lobe color: Upper surface: RHS 67A. Lower surface: RHS 67B. Corolla tube color: Inner: RHS N77A. Outer: RHS N77A.
*Conspicuousness of the veins on the upper surface of the corolla lobe.*—Medium.
*Fragrance.*—Absent.

Reproductive organs:
*Stamen number.*—5.
*Stamen color.*—Anther color: RHS 7B. Anther shape: Ellipsoidal. Anther length: 0.7 mm. Filament color: RHS 10B. Filament length: 8.0 mm. Pollen color: RHS 7B. Pollen amount: Scarce.
*Ovary.*—Placenta arrangement: Ovate. Ovary color: RHS N144C. Pistil number: 1. Pistil length: 0.1 cm. Stigma color: RHS 154A. Style length: 0.9 cm. Style color: RHS 149B.
*Fruit/seed set.*—Small quantity; description of seed not available.

Disease/insect resistance: None observed.

COMPARISON WITH PARENTAL LINES AND KNOWN VARIETY

'KLECA13248' is distinguished from its parental lines as described in Table 1:

TABLE 1

Comparison with Parental Lines

| Trait | Variety 'KLECA13248' | Female parent 'KLECA08170' | Male Parent 'CA-2008-0300' |
|---|---|---|---|
| Flower color | Red-purple | Light blue | Red |

'KLECA13248' is most similar to the *Calibrachoa* plant named 'KLECA10218' (U.S. Plant Pat. No. 22,892). Differences between the two varieties are described in Table 2:

TABLE 2

Comparison with Similar Variety

| Trait | Variety 'KLECA13248' | Commercial line 'KLECA10218' |
|---|---|---|
| Habit | Semi-trailing | Semi-upright |

We claim:

1. A new and distinct variety of *Calibrachoa* plant named 'KLECA13248' as illustrated and described herein.

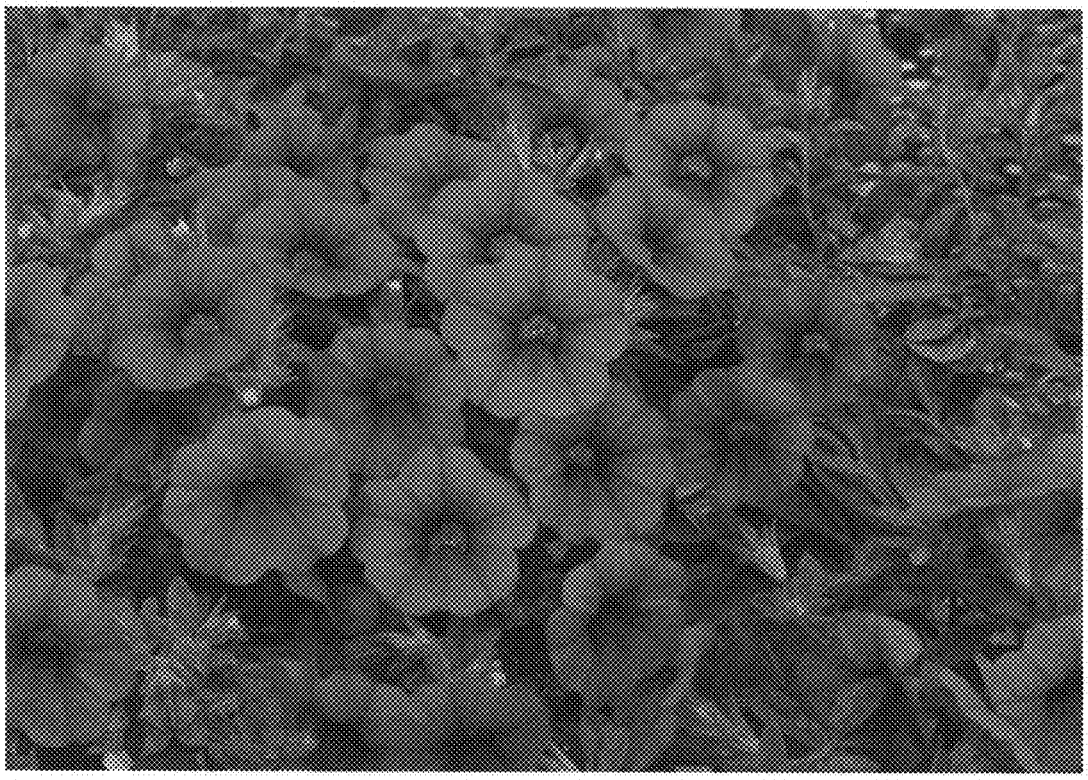

* * * * *